| United States Patent [19] | [11] Patent Number: 4,982,003 |
|---|---|
| Hara et al. | [45] Date of Patent: Jan. 1, 1991 |

[54] MIXED OXIDE CATALYST AND PROCESS FOR PRODUCING AN ALKYLENAMINE BY USING THE CATALYST

[75] Inventors: Yasushi Hara; Nobumasa Suzuki, both of Shin-nanyo; Yukio Ito, Kudamatsu; Kazuhiko Sekizawa, Shin-nanyo, all of Japan

[73] Assignee: Tosoh Corporation, Shinnanyo, Japan

[21] Appl. No.: 266,163

[22] Filed: Nov. 2, 1988

[30] Foreign Application Priority Data

| Nov. 6, 1987 [JP] | Japan | 62-279097 |
| Nov. 13, 1987 [JP] | Japan | 62-285403 |
| Nov. 17, 1987 [JP] | Japan | 62-288405 |
| Nov. 19, 1987 [JP] | Japan | 62-290651 |
| Feb. 10, 1988 [JP] | Japan | 63-27490 |

[51] Int. Cl.$^5$ .......................................... C07C 209/00
[52] U.S. Cl. ...................................... 564/480; 564/479
[58] Field of Search ................. 564/480, 479; 502/202, 502/209, 206; 546/184

[56] References Cited

U.S. PATENT DOCUMENTS

| 2,389,500 | 11/1945 | Goshorn | 564/480 |
| 3,714,529 | 1/1973 | Lichtenwalter et al. | 564/480 |
| 4,046,780 | 9/1977 | Nakanishi et al. | 549/248 |
| 4,269,737 | 5/1981 | Grenoble et al. | 252/464 |
| 4,289,656 | 9/1981 | Hayes et al. | 252/470 |
| 4,448,997 | 5/1984 | Brennan | 564/479 |
| 4,613,705 | 9/1986 | Hargis | 564/409 |

FOREIGN PATENT DOCUMENTS 0168811 1/1986 European Pat. Off. .

Primary Examiner—Glennon H. Hollrah
Assistant Examiner—Brian Bembenick
Attorney, Agent, or Firm—Oblon, Spivak, McClelland, Maier & Neustadt

[57] ABSTRACT

A mixed oxide catalyst comprising niobium oxide and a member selected from the group consisting of titania, alumina, silica, zirconia and oxides of elements in Groups IIA, VA, VIA, IB, IIB, IIIB, VB, VIB, VIIB and VIII of the Periodic Table. A process for producing an alkylenamine, which comprise reacting ammonia and/or an alkylenamine with an alkanolamine in the presence of such a mixed oxide.

8 Claims, No Drawings

MIXED OXIDE CATALYST AND PROCESS FOR PRODUCING AN ALKYLENAMINE BY USING THE CATALYST

The present invention relates to a mixed oxide catalyst and a process for producing an alkylenamine using such a mixed oxide catalyst.

Heretofore, a number of industrial processes are known wherein sulfuric acid, phosphoric acid, aluminum chloride, etc. are used as acid catalysts. In general, when such a catalyst is used in a system where water is present, for example, in a homogeneous system with such a catalyst dissolved in water, it is difficult to separate the catalyst from the reaction product, and there will be a problem such as corrosion of the apparatus. Whereas in the case of a heterogeneous system, there is a problem in the useful life of the catalyst, such as a decrease in the activities due to flowing away of the catalyst, and there still remains a problem of corrosion of the apparatus just like in the case of the homogeneous system. Under the circumstances, various studies have been made for solid acids as acid catalysts, and ion exchange resins have been proposed as solid acid catalysts which are hardly decomposed in a system where water is present. However, such ion exchange resins are expensive, and they are inferior in the heat resistance. As a solid acid catalyst useful in the presence of water, Japanese Unexamined Patent Publication No. 44039/1975 discloses a water-containing niobium oxide. However, this catalyst is also inadequate in the heat resistance from the industrial point of view, since the activities deteriorate substantially at a temperature of 500° C. or higher.

On the other hand, as a process for producing alkylenamines, particularly ethylenamines which are particularly important from the industrial point of view, a process is known wherein ethylene dichloride is reacted with ammonia. By this process, the production of piperazine and piperazine ring-containing cyclic ethylenamines is small. Namely, it is possible to obtain ethylenamines having high non-cyclic rates and industrially preferred quality. This process is practically widely used. However, it has a problem that a large amount of sodium chloride is formed as a by-product, and its separation and treatment are costly.

Another process wherein a monoethanolamine is used as starting material, and ammonia is reacted thereto in the presence of hydrogen and a hydrogenation catalyst to obtain an ethylamine, is also widely practically employed. However, piperazine ring-containing cyclic ethylenamines which are undesirable from the viewpoint of quality, are produced in a substantial amount although ethylenediamines may be produced with high efficiency. Therefore, it is difficult to produce polyethylenepolyamines having high molecular weights.

In addition to these processes, a process has been proposed wherein monoethanolamine is used as starting material, and ammonia or/and ethylenamine are reacted thereto by using a phosphorus-containing substance as catalyst to produce an ethylenamine. For example, Japanese Unexamined Patent Publication No. 147600/1976 discloses a process wherein phosphoric acid or phosphorous acid is used as catalyst. However, these catalysts are soluble in the reaction solution containing water. Therefore, a special step for the separation and recovery from the reaction solution is required. Under the circumstances, processes for the production of ethylenamines have been proposed wherein various salts of phosphoric acid and supported phosphoric acid insoluble in the reaction solution containing water are used as catalysts. U.S. Pat. No. 4,448,997 discloses a process for producing ethylenamines wherein aluminum phosphate is used as catalyst, and Japanese Unexamined Patent Publication No. 41641/1985 discloses such a process wherein a phosphate of a metal of Group IIIb such as lanthanum phosphate is used as catalyst. Further, Japanese Unexamined Patent Publication No. 150538/1984 discloses a process wherein phosphoric acid supported on e.g. titanium dioxide is used as catalyst. However, these phosphates and supported phosphoric acid are substantially poorer in the catalytic activities than free phosphoric acid. Further, by the use of these phosphoric acid type catalysts, it is not possible to reduce piperazine ring-containing cyclic amines undesirable from the viewpoint of quality to a level sufficiently low for the industrial purpose. As a phosphoric acid catalyst having high activities, there is a phosphorus-containing ion exchanger resin. However, this catalyst is poor in the heat resistance and thus has a problem in the catalytically useful life.

As a non-phosphorus catalyst, silica-alumina is disclosed in Japanese Unexamined Patent Publication No. 38329/1980, but the catalytic activities of this catalyst are very low.

As described in the foregoing, some solid acid catalysts have been disclosed as catalysts which may be used in a system containing water. However, they have a problem that they are inferior in the heat resistance, and they are still inadequate from the industrial point of view. Therefore, it is desired to develop a solid acid catalyst useful in a system containing water, which is excellent in the heat resistance.

As described above, many processes have been disclosed for the production of alkylenamines. However, such processes are still inadequate from the industrial point of view. Particularly it is desired to develop a process for producing high quality alkylenamines having high non-cyclic rates by using a solid catalyst having high catalytic activities and high heat resistance and being hardly soluble in the reaction solution, for the production of alkylenamines using alkanolamines as starting material.

Under these circumstances, the present inventors have conducted extensive researches on solid acids. As a result, they have found that a mixed oxide comprising niobium oxide and titania, niobium oxide and alumina, niobium oxide and silica, niobium oxide and zirconia, and niobium oxide and an oxide of an element in Group IIA, VA, VIA, IB, IIB, IIIB, VB, VIB, VIIIB or VIII of the Periodic Table are solid acids which are hardly soluble in water and have excellent heat resistance. The present invention has been accomplished on the basis of this discovery.

Further, the present inventors have conducted extensive researches on a process for producing alkylenamines having alkylene chains increased over ammonia and/or alkylenamines as starting material by the reaction of the ammonia and/or alkylenamines with alkanolamines. As a result, they have found that a mixed oxide catalyst comprising niobium oxide and titania, niobium oxide and alumina, niobium oxide and silica, niobium oxide and zirconia, or niobium oxide and an oxide of an element in Group IIA, VA, VIA, IB, IIB, IIIB, VB, VIB, VIIB or VIII of the Periodic Table, has high activities as catalyst and is a solid hardly soluble in a reaction solution containing water, and it is also excellent in the heat resistance. The present invention has been accomplished on the basis of these discoveries.

The present invention provides a mixed oxide catalyst comprising niobium oxide and a member selected from the group consisting of titania, alumina, silica, zirconia and oxides of elements in Groups IIA, VA, VIA, IB, IIB, IIIB, VB, VIB, VIIB and VIIIB of the Priodic Table.

The present invention also provides a process for producing an alkylenamine, which comprises reacting ammonia and/or an alkylenamine with an alkanolamine in the presence of such a mixed oxide catalyst to obtain an alkylenamine having an increased number of alkylene chains over the ammonia and/or the alkylenamine as starting material.

Now, the present invention will be described in further detail.

The catalyst used in the present invention is a mixed oxide comprising niobium oxide and titania, niobium oxide and alumina, niobium oxide and silica, niobium oxide and zirconia, or niobium oxide and an oxide of an element in Group IIA, VA, VIA, IB, IIB, IIIB, VB, VIB, VIIB or VIII of the Periodic Table. The mixed oxide catalyst is a substance obtained by converting a compound containing niobium and a compound containing titanium, aluminium, silicon, zirconium or an element in Group IIA, VA, VIA, IB, IIB, IIIB, VB, VIB, VIIB or VIII of the Periodic Table simultaneously to the oxide or hydroxide of niobium and to the oxide or hydroxide of titanium, aluminium, silicon, zirconium or an element in Group IIA, VA, VIA, IB, IIB, IIIB, VB, VIB, VIIB or VIII of the Periodic Table. There is no particular restriction as to the oxidized state of niobium, and it may be pentavalent, tetravelent, trivalent, bivalent or monovalent. However, tetravalent niobium is preferred. Titaniux, silicon and zirconium are preferably tetravalent, and aluminum is preferably trivalent.

The mixed oxide to be used in the present invention may be used alone by itself, or may be combined with other substance in the form of a mixture or in the form of a mixed oxide with other oxide.

The mixed oxide catalyst can be obtained by converting a compound containing niobium and a compound containing titanium, aluminium, silicon, zirconium or an element of Group IIA, VA, VIA, IB, IIB, IIIB, VB, VIB, VIIB or VIII of the Periodic Table simultaneously to the oxide or hydroxide of niobium and to the oxide or hydroxide of titanium, aluminum, silicon, zirconium or an element in Group IIA, VA, VIA, IB, IIB, IIIB, VB, VIB, VIIB or VIII of the Periodic Table. Various methods are available for the conversion, including:

(1) A method wherein the pH of a solution of a niobium-containing compound and a compound containing titanium, aluminum, silicon, zirconium or an element in Group IIA, VA, VIA, IB, IIB, IIIB, VB, VIB, VIIB or VIII of the Periodic Table is changed to convert them to insoluble hydroxides, which are then dehydrated to obtain a mixed oxide;

(2) A method wherein an organic substance such as an alkoxide of niobium and an organic substance such as an alkoxide of titanium, aluminum, silicon, zirconium or an element in Group IIA, VA, VIA, IB, IIB, IIIB, VB, VIB, VIIB or VIII of the Periodic Table, are hydrolyzed; and (3) A method wherein an organic substance such as an alkoxide of niobium and an organic substance such as an alkoxide of titanium, aluminum, silicon, zirconium or an element in Group IIA, VA, VIA, IB, IIB, IIIB, VB, VIB, VIIB or VIII of the Periodic Table, are thermally decomposed. Any one of such methods may be employed.

The ratio of the respective components of the mixed oxide to be used in the present invention is as follows. The molar ratio of niobium to titanium (Nb/Ti) is from 0.01 to 100, preferably from 0.1 to 100, more preferably from 0.1 to 10. The molar ratio of niobium to aluminum (Nb/Al), niobium to silicon (Nt/Si), or niobium to zirconium (Nb/Zr) is from 0.001 to 100, preferably from 0.01 to 100, more preferably from 0.01 to 10. The molar ratio of the niobium to an element in Group IIA, VA, VIA, IB, IIB, IIIB, VB, VIB, VIIB or VIIIB of the Periodic Table substantially varies depending upon the element and may not generally be defined. For example, in the case of Ca in Group IIA in the Periodic Table, the molar ratio of Nb/Ca is from 10 to 1,000. In the case of Bi in Group VA, the molar ratio of Nb/Bi is from 0.1 to 1,000. In the case of Te in Group VIA, the molar ratio of Nb/Te is from 0.1 to 1,000. In the case of Cu in Group IB, the molar ratio of Nb/Cu is from 0.1 to 1,000. In the case of Zn in Group IIB, the molar ratio of Nb/Zn is from 0.1 to 1,000. In the case of La in Group IIIB, the molar ratio of Nb/La is from 0.01 to 100. In the case of Ta in Group VB, the molar ratio of Nb/Ta is from 0.001 to 1,000. In the case of Cr in Group VIB, the molar ratio of Nb/Cr is from 0.1 to 1,000. In the case of Mn in Group VIIB, the molar ratio of Nb/Mn is from 0.1 to 1,000. In the case of Fe in Group VIII, the molar ratio of Nb/Fe is from 0.1 to 1,000. If Nb is less than these ranges, the quality of the resulting alkylenamine tends to be inferior, and if it exceeds the above ranges, the heat resistance of the catalyst tends to deteriorate.

In the present invention, there is no particular restriction as to the shape of the catalyst. Depending upon the reaction system, it may be used as powder, or may be used in a molded form. For example, in a suspension bed system, it is used in a powder or granular form. In a fixed bed system, it is used in a molded form of pellets or beads.

The molding method of the catalyst includes extrusion molding, tablet molding or granule molding. For the molding, silica, alumina, alumina-silica, clay or the like may be added as a binder.

Further, in order to increase the surface area of the catalyst, the mixed oxide may te supported on a carrier such as silica, alumina, titania, zirconia or porous vycor glass.

The catalyst may be used after calcination or without sintering. When calcination is applied, there is no particular restriction as to the calcination temperature. However, the calcination temperature is preferably not higher than 700° C. If calcination is conducted at a temperature exceeding 700° C., the surface area tends to be small, whereby the catalytic activities tends to be reduced.

The amount of the mixed oxide catalyst used in the present invention may be at and level so long as it is sufficient to have the reaction proceeded at an industrially useful reaction rate.

Ammonia or the alkylenamine to be used in the process of the present invention is a compound represented by the formula I:

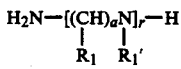 (I)

wherein a is a number of from 2 to 6, r is a number of from 0 to 6, $R_1$ is hydrogen or an alkyl group having from 1 to 4 carbon atoms, $R_1'$ is a group represented by the formula (1):

$$-[(CH_2)_b(NH)_d]_s-H \quad (1)$$

wherein b is a number of from 2 to 6, d is 0 or 1, and s is a number of from 0 to 4, or a compound represented by the formula (2):

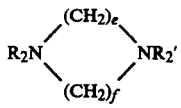 (II)

wherein e is a number of from 2 to 6, f is a number of from 2 to 6, and each of $R_2$ and $R_2'$ is a group represented by the formula (2):

$$-[(CH_2)_gNH]_t-H \quad (2)$$

wherein g is a number of from 2 to 6, and t is a number of 0 to 5.

Either the compound of the formula I or the compound of the formula II may be employed. Preferably, however, ammonia or an alkylenamine of the formula I is employed. When an alkylenamine of the formula I is used, a high quality alkylenamine having a high no-cyclic rate is obtainable. Ammonia and the alkylenamine of the formula I include ammonia, ethylenamines such as ethylenediamine, diethylenetriamine, triethylenetetramine, tetraethylenepentamine, pentaethylenehexamine and hexaethyleneheptamine, propyleneamines such as propylenediamine and dipropylenetriamine, butyleneamines such as butylenediamine and dibutylenetriamine, alkylenamines such as hexamethylenediamine and alkylated products thereof such as N-methylethylenediamine and N-ethylethylenediamine. Among them ethylenamines such as ethylenediamine and diethylenetriamine are preferred as starting material to be used in the process of the present invention.

Ammonia and alkylenamines to be used in the process of the present invention may be used alone or in combination as a mixture of two or more different kinds.

The alkanolamine to be used in the process of the present invention is a compound represented by the formula III:

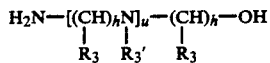 (III)

wherein h is a number of from 2 to 6, u is a number of from 0 to 5, $R_3$ is hydrogen or an alkyl group having from 1 to 4 carbon atoms, and $R_3'$ is a group represented by the formula (3):

$$-[(CH_2)_i-(NH)_j]_v-H \quad (3)$$

wherein i is a number of from 1 to 6, j is 0 or 1, and v is a number of from 0 to 4, or a compound represented by the formula IV:

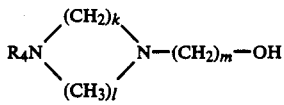 (IV)

wherein k is a number of from 2 to 6, 1 is a number of from 2 to 6, m is a number of from 2 to 6, and $R_4$ is a group represented by the formula (4):

$$-[(CH_2)_n-NH]_w-H \quad (4)$$

wherein n is a number of from 2 to 6, and w is a number of from 0 to 5.

Either the compound of the formula III or the compound of the formula IV may be employed. However, the alkanolamine of the formula III is preferably employed. When the alkanolamine of the formula III is used, a high quality alkylenamine having a high no-cyclic rate is obtainable. The alkanolamine cf the formula III includes alkanolamines such as monoetharolamine, N-(2-aminoethyl)ethanolamine, monopropanolamine and N-(3-aminopropyl)propanolamine. As the starting material to be used in the process of the present invention, ethanolamines such as monoethanolamine and N-(2-aminoethyl)ethanolamine are preferred.

The alkanolamines to be used in the process of the present invention may be used alone or in combination as a mixture of two or more different kinds.

The combination of starting materials supplied for the reaction in the process of the present invention includes the following three types:

(1) Ammonia and an alkanolamine;
(2) An alkylenamine and an alkanolamine; and
3) Ammonia, an alkylenamine and an alkanolamine. The reaction may be conducted any one of such combinations.

Preferred combinations of starting materials include:
(1) Ammonia and an alkanolamine of the formula III;
(2) An alkylenamine of the formula I other than ammonia and an alkanolamine of the formula III; and
(3) Ammonia and an alkylenamine of the formula I and an alkanolamine of the formula III. More preferred combinations of starting materials include:
(1) Ammonia and an ethanolamine;
(2) An ethylenamine and an ethanolamine; and
(3) Ammonia, an ethylenamine and an ethanolamine.

Preferred molar ratios of the starting materials to be supplied in the process of the present invention are as follows:

(1) In the case where ammonia and an alkanolamine are used as starting materials, the molar ratio of ammonia/the alkanolamine is from 2 to 30;
(2) In a case where an alkylenamine and an alkanolamine are used as starting materials, the molar ratio of the alkylenamine/the alkanolamine is from 0.5 to 10; and
(3) In a case where ammonia, an alkylenamine and an alkanolamine are used as starting materials, the molar ratio of (ammonia+the alkylenamine)/the alkanolamine is from 0.5 to 30.

In each case, the quality of the resulting alkylenamine varies depending upon the molar ratio of the starting materials. If the molar ratio is smaller than the above-mentioned ranges, piperazine ring-containing amines will be produced in a substantial amount, whereby alkylenamines having undesirable quality tend to form. If the molar ratio is larger than the above range, the reaction rate tends to decrease, and the pressure is required to be extremely high, such being not practical.

In the process of the present invention, the resulting alkylenamine differs depending upon the types of the starting materials. When an alkanolamine is reacted to ammonia and/or an alkylenamine, the resulting alkylenamine has alkylene chains increased over the ammonia or the alkylenamine as starting material. Namely, when the alkanolamine of the formula III is reacted to the ammonia and/or the alkylenamine of the formula I, the resulting alkylenamine will be a compound represented by the formula V:

wherein o is a number of from 2 to 6, x is a number of 1 to 7, $R_5$ is hydrogen or an alkyl group having from 1 to 4 carbon atoms, and $R_5'$ is a group of the formula (5):

wherein p is a number of from 1 to 6, q is 0 or 1, and y is a number of 0 to 4, wherein x and/or y in the resulting alkylenamine is a number larger at least by one than r and/or s of the ammonia or the alkylenamine as starting material. Thus, an alkylenamine having an increased number of alkylene chains over the starting material is obtainable. For example, when ammonia is reacted with monoethanolamine, ethylenediamine and non-cyclic polyethylenepolyamines such as diethylenetriamine, triethylenetetramine, tetraethylenepentamine and pentaethylenehexamine will be formed. When ethylenediamine is reacted with monoethanolamine, the above-mentioned non-cyclic polyethylenepolyamines will be formed. When ammonia and ethylenediamine are reacted with monoethanolamine, ethylenediamine and the above-mentioned non-cyclic polyethylenepolyamires will be formed.

In the process of the present invention, the reaction is conducted usually at a temperature within a range of from 200° to 400° C., preferably from 240° to 350° C. If the temperature is less than 200° C., the reaction rate tends to be substantially low, and if it exceeds 400° C., the resulting alkylenamine tends to undergo decomposition, such being not practical.

In the process of the present invention, the reaction may be conducted in a gas phase or in a liquid phase. However, it is preferred to conduct it in a liquid phase in order to produce a high quality alkylenamine.

In the process of the present invention, the reaction may be conducted by a suspended batch, semi-batch or continuous system, or by a fixed bed system. However, the fixed bed system is industrially advantageous from the viewpoint of the operation, apparatus and economy.

In the process of the present invention, the pressure for the reaction varies substantially depending upon whether the reaction is a gas phase reaction or a liquid phase reaction, or whether or not ammonia is used. Therefore, it is difficult to define the pressure range. However, for example, in the case of a liquid phase reaction using no ammonia, the pressure is within a range of from about 1 to about 300 kg/cm²G.

In the process of the present invention, the catalyst will usually be separated and recovered from the reaction solution, and then the starting material is separated and recovered by distillation. The separated and recovered starting material is recycled to the reaction zone, as the case requires. A part of the reaction product may be recycled to the reaction zone in order to change the composition of the reaction product. The separation of the starting material and the product is usually conducted by distillation. Such distillation may be conducted by a continuous system or by a batch system.

The reaction product may be treated with active carbon or sodium borohydride in order to improve the purity or color tone of the reaction product. The color tone, odor, etc. of the reaction product may be improved by conducting the reaction in the presence of hydrogen.

The formed water may be removed from the reaction zone in order to reduce the formation of amines undesirable from the viewpoint of quality such as hydroxyl group-containing amines or to improve the reaction rate. Otherwise, the reaction may be conducted with an addition of water in order to prolong the catalytically useful life or to make it easy to handle ammonia or the alkylenamine.

The mixed oxide catalyst of the present invention is stable in a system containing water and excellent in the heat resistance, and thus it is industrially very useful. Further, the present invention provides a process for producing a high quality alkylenamine in good yield by using a mixed oxide catalyst, which is highly active, resistant to corrosion by the reaction solution and excellent in the heat resistance, and thus it is industrially extremely significant.

Now, the present invention will be described in further detail with reference to Examples. However, it should be understood that the present invention is by no means restricted to such specific Examples.

Alkylenamines as reaction products and alkylenamines and alkanolamines as starting materials will be represented by the following abbreviations:
 EDA: Ethylenediamine
 MEA: Monoethanolamine
 PIP: Piperazine
 AEP: N-(2-aminoethyl)piperazine
 DETA: Diethylenetriamine
 AEEA: N-(2-aminoethyl)ethanolamine
 TETA: Triethylenetetramine (linear, branched or cyclic isomer)
 TEPA: Tetraethylenepentamire (linear, branched or cyclic isomer)

EXAMPLE 1: PREPARATION OF CATALYSTS
Catalyst 1

Into a 500 ml of flask, 15.3 g (48.1 mmol) of niobium pentaethoxide and 13.6 g (48.1 mmol) of titanium tetraisopropoxide were charged under a nitrogen stream and dissolved in 40 ml of 1-butanol. This solution was refluxed, and 300 ml of water was dropwise added thereto under stirring. Formed precipitates were collected by filtration and washed with water. They were calcined at 400° C. for 2 hours under a dry air stream to obtain an niobium-titania mixed oxide. As a result of the elemental analysis, the molar ratio of Nt/Ti was 1. The BET specific surface area thereof was 309 m²/g. The mixed oxide was not crystallized, and no X-ray diffraction pattern was observed in the X-ray diffraction analysis. To the niobium-titanium mixed oxide catalyst, 100 ml of distilled water was added, and the mixture was refluxed for 2 hours. Then, the catalyst was collected by filtration and calcined at 400° C. under a dry air stream, whereby the mixed oxide was recovered 100%.

Catalyst 2

10.0 g (37 mmol) of niobium pentachloride and 7.2 g (38 mmol) of titanium chloride were dissolved in 50 ml of methanol. To this solution, 200 ml of 7% aqueous ammonia was added. Formed precipitates were collected by filtration, washed with water and then calcined at 400° C. for 2 hours under a dry air stream. The BET specific surface area was 45 m$^2$/g. As a result of the elemental analysis, the molar ratio of Nt/Ti was 1.

Catalyst 3

25.2 g (79 mmol) of niobiux pentaethoxide and 2.5 g (8.8 mmol) of titanium tetraiscpropoxide were dissolved in 20 ml of 1-butanol, and the solution was refluxed. To this solution, 350 ml of water was dropwise added. Formed precipitates were collected by filtration, washed with water and then calcined at 400° C. for 2 hours under a dry air stream. The BET specific surface area was 295 m$^2$/g. As a result of the elemental analysis, the molar ratio of Nb/Ti was 9.

Catalyst 4

10.5 g (33 mmol) of niobiux pentaethoxide and 84.4 g (297 mmol) of titanium tetraiscpropoxide were dissolved in 20 ml of 1-butanol, and the solution was refluxed. To this solution, 350 ml of water was dropwise added. Formed precipitates were collected by filtration, washed with water and calcined at 400° C. for 2 hours under a dry air stream. As a result of the elemental analysis, the molar ratio of Ti/Nb was 9. The BET surface area was 179 m$^2$/g.

Catalyst 5

Catalyst 1 was calcined at 600° C. for 2 hours under a dry air stream. The BET specific surface area was 110 m$^2$/g. From the X-ray diffration, this catalyst was found to be not crystallized.

Catalyst 6

Into a 500 ml flask, 13.2 g (41.5 mmol) of niobium pentaethoxide and 8.5 g (41.8 mmol) of aluminum isopropoxide were introduced under a nitrogen stream and dissolved in 1-butanol under reflux. Then, 300 ml of water was dropwise added thereto over a period of 20 minutes, and the mixture was heated for one hour and 40 minutes. The mixture was left to stand still overnight. Then, formed precipitates were collected by filtration and washed with water. They were calcined at 400° C. for 2 hours to obtain a catalyst. As a result of the elemental analysis, the molar ratio of Nb/Al was 1. The BET specific surface area thereof was 296 m$^2$/g. This mixed oxide was not crystallized, and no X-ray diffraction pattern was observed by the X-ray diffraction analysis. To this oxidized niobium-alumira mixed oxide catalyst, 100 ml of distilled water was added, and the mixture was refluxed for 2 hours. Then, the catalyst was collected by filtration and calcined at 400° C. under a dry air stream, whereby the mixed oxide was recovered 100%.

Catalyst 7

10.0 (37 mmol) of niobium pentachloride an 4.9 g (37 mmol) of aluminum chloride were dissolved in 50 ml of methanol. To this solution, 7% aqueous ammonia was added until the solution became pH 7. Formed precipitates were collected by filtration, washed with water and calcined at 400° C. for 2 hours under a dry air stream to obtain a catalyst, which is designated is Catalyst 7. As a result of the elemental analysis, the molar ratio of Nb/Al was 1.

Catalyst 8

Under a nitrogen stream, 20.0 g (62.9 mmol) of niobium pentaethoxide and 1.4 g (6.85 mmol) of aluminum isopropoxide were dissolved in 1-butanol under reflux. To this mixture, 300 ml of water was dropwise added over a period of 20 minutes, and the mixture was heated for one hour and 40 minutes. The mixture was left to stand overnight. Then, formed precipitates were collected by filtration and washed with water. Then, they were calcined at 400° C. for 2 hours to obtain a catalyst, which is designated as Catalyst 8. As a result of the elemental analysis, the molar ratio of Nt/Al was 9.

Catalyst 9

Under a nitrogen stream, 5.0 g (15.7 mmol) of niobium pentaethoxide and 28.9 g (141 mmol) of aluminum isopropoxide were dissolved in 1-butanol under reflux. To this solution, 300 ml of water was dropwise added. Formed precipitates were collected by filtration, washed with water and calcined at 400° C. for 2 hours under a dry air stream to obtain a catalyst, which is designated as Catalyst 9. As a result of the elemental analysis, the molar ratio of Nb/Al was 0.11.

Catalyst 10

Under a dry air stream, Catalyst 6 was calcined at 600° C. for 2 hours to obtain a catalyst which is designated as Catalyst 10. The BET specific surface area was 195 m$^2$/g.

Catalyst 11

Into a 500 ml flask, 13.0 g (40.9 mmol) of niobium pentaethoxide and 8.51 g (40.9 mmol) of tetraethoxysilane were introduced under a nitrogen stream and dissolved in 40 ml of 1-butanol. This solution was refluxed, and 200 ml of water was dropwise added thereto over a period of 40 minutes. The heating was continued for further 35 minutes, and then the mixture was cooled and left to stand overnight. The supernatant was removed, and formed precipitates were collected by filtration and washed with water. The precipitates were calcined at 400° C. for 2 hours under a dry air stream to obtain a catalyst, which is designated as Catalyst 11. As a result of the elemental analysis, the molar ratio of Nb/Si was 1. The BET specific surface area was 274 m$^2$/g. This mixed oxide was not crystallized, and no X-ray diffraction pattern was observed by the X-ray diffraction analysis. To the oxidized niobium-silica mixed oxide catalyst, 100 ml of distilled water was added, and the mixture was refluxed for 2 hours. Then, the catalyst was collected by filtration and calcined at 400° C. under a dry air stream, whereby the mixed oxide was recovered 100%.

Catalyst 12

5.2 g (16.3 mmol) of niobium pentaethoxide and 45.3 g (297.4 mmol) of tetramethoxysilane were dissolved in 50 ml of methanol, and the solution was refluxed. To this solution, 50 ml of water was dropwise added in 10 minutes, and then the mixture was refluxed for 30 minutes. The mixture was left to stand overnight, and then the solvent was distilled off. The residue was dried at 130° C. for 16 hours to obtain a catalyst, which is designated as Catalyst 12. As a result of the elemental analysis, the molar ratio of Nb/Si was 0.055.

Catalyst 13

15.9 g (49.9 mmol) of niobium pentaethoxide and 1.15 g (5.5 mmol) of tetraethoxysilane were dissolved in 1-butanol, and the solution was refluxed. To this solution, 500 ml of water was dropwise added. After the dropwise addition, the refluxing was continued for 1.5 hours. Then, formed precipitates were collected by filtration, washed with water and calcined at 300° C. for 2 hours to obtain a catalyst which is designated as Catalyst 13. As a result of the elemental analysis, the molar ratio of Nb/Si was 9.1.

Catalyst 14

10.0 g (37 mmol) of niobium pentachloride and 6.3 g (37 mmol) of silicon tetrachloride were dissolved in 50 ml of methanol. To this solution, 200 ml of 7% aqueous ammonia was added. Formed precipitates were collected by filtration, washed with water and calcined at 400° C. for 2 hours under a dry air stream to obtain a catalyst, which is designated as Catalyst 14. The BET specific surface area was 45 m$^2$/g. As a result of the elemental analysis, the molar ratio of Nb/Si was 1.

Catalyst 15

Catalyst 11 was calcined at 600° C. for 2 hours under a dry air stream to obtain a catalyst, which is designated as Catalyst 15. The BET specific surface area was 113 m$^2$/g.

Catalyst 16

Into a 500 ml flask, 13.5 g (42.4 mmol) of niobium pentaethoxide and 16.5 g (43.0 mmol) of zirconium tetrabutoxide were charged under a nitrogen stream and dissolved in 1-butanol under reflux. To the solution, 300 ml of water was dropwise added over a period of one hour and 20 minutes. The mixture was heated for further one hour and 20 minutes. The mixture was left to stand still overnight. Then, formed precicipitates were collected by filtration and washed with water. They were calcined at 400° C. for 2 hours to obtain a catalyst, which is designated as Catalyst 16. As a result of the elemental analysis, the molar ratio of Nb/Zr was 1. The BET specific surface area was 241 m$^2$/g. This mixed oxide was not crystallized, and no X-ray diffraction pattern was observed by the X-ray diffraction analysis. To the oxidized niobium-zirconia mixed oxide catalyst, 100 ml of distilled water was added, and the mixture was refluxed for 2 hours. Then, the catalyst was collected by filtration and calcined at 400° C. under a dry air stream, whereby the mixed oxide was recovered 100%.

Catalyst 17

10.0 g (37 mmol) of niobium pentachloride and 8.6 g (37 mmol) of zirconium chloride were dissolved in 50 ml of methanol. To this solution, 7% aqueous ammonia was added until the solution became pH 7. Formed precipitates were collected by filtration, washed with water and calcined at 400° C. for 2 hours under a dry air stream to obtain a catalyst, which is designated as catalyst 17. As a result of the elemental analysis, the molar ratio of Nb/Zr was 1.

Catalyst 18

Under a nitrogen stream, 20.0 g (62.9 mmol) of niobium pentaethoxide and 2.7 g (7.04 mmol) of zirconium tetrabutoxide were added to 1-tutanol and dissolved under reflux. To this solution, 300 ml of water was dropwise added over a period of 20 minutes, and the mixture was heated for further one hour and 40 minutes. The mixture was left to stand still overnight, and formed precipitates were collected by filtration and washed with water. They were calcined at 400° C. for 2 hours to obtain a catalyst, which is designated as Catalyst 18. As a result of the elemental analysis, the molar ratio of Nb/Zr was 9.

Catalyst 19

Under a nitrogen stream, 5.0 g (15.7 mmol) of niobium pentaethoxide and 54.2 g (141 mmol) of zirconium tetrabutoxide were added to 1-butanol and dissolved under reflux. To this solution, 300 ml of water was dropwise added. Formed precipitates were collected by filtration, washed with water and calcined at 400° C. for 2 hours under a dry air stream to obtain a catalyst, which is designated as Catalyst 19. As a result of the elemental analysis, the molar ratio of Nb/Zr was 0.11.

Catalyst 20

Under a dry air stream, Catalyst 16 was calcined at 600° C. for 2 hours to obtain a catalyst, which is designated as Catalyst 20. The BET specific surface area was 152 m$^2$/g.

Catalyst 21

5 g of niobium pentachloride was dissolved in 10 ml of methanol. To this solution, a solution obtained by dissolving 2 g of calcium chloride in 50 ml of water, was added. Further, the mixture was diluted with 300 ml of water, and 50 ml of 15% aqueous ammonia was dropwise added thereto. Formed precipitates were collected by filtration, washed with water and calcined at 400° C. for 2 hours under a dry air stream to obtain a catalyst, which is designated as Catalyst 21.

Catalyst 22

5 g of niobium pentachloride and 5.8 g of bismuth trichloride were dissolved in 100 ml of methanol. This solution was dropwise added to 100 ml of 15% aqueous ammonia. Formed precipitates were collected by filtration, washed with water and calcined at 400° C. for 2 hours under a dry air stream to obtain a catalyst, which is designated as Catalyst 22.

Catalyst 23

5 g of niobium pentachloride and 5 g of tellurium tetrachloride were dissolved in 100 ml of methanol. This solution was dropwise added to 100 ml of 15% aqueous ammonia. Formed precipitates were collected by filtration, washed with water and calcined at 400° C. for 2 hours under a dry air stream to obtain a catalyst, which is designated as Catalyst 23.

Catalyst 24

5 g of niobium pentachloride and 3.1 g of copper (II) chloride dihydrate were dissolved in methanol. The solution was dropwise added to 300 ml of a 2% sodium hydroxide aqueous solution. Formed precipitates were collected by filtration, washed with water and calcined at 400° C. for 2 hours under a dry air stream to obtain a catalyst, which is designated as Catalyst 24.

Catalyst 25

5 g of niobium pentachloride was dissolved in 10 ml of methanol. To this solution, a solution prepared by dissolving 2.5 g of zinc (II) chloride in 100 ml of water, was added. This solution was dropwise added to 350 ml of a 2% sodium hydroxide aqueous solution. Formed precipitates were collected by filtration, washed with water and calcined at 400° C. for 2 hours under a dry air stream to obtain a catalyst, which is designated as Catalyst 25.

Catalyst 26

5 g of niobium pentachloride was dissolved in 10 ml of methanol. To this solution, a solution prepared by dissolving 8 g of lanthanum nitrate hexahydrate in 50 ml of water, was added. This mixture was diluted with 300 ml of water, and 100 ml of 15% aqueous ammonia was added thereto. Formed precipitates were collected by filtration, washed with water and calcined at 400° C. for 2 hours under a dry air stream to obtain a catalyst, which is designated as Catalyst 26.

Catalyst 27

5 g of tantalum pentachloride and 15 g of niobium pentachloride were dissolved in 500 ml of methanol. The solvent was distilled off under reduced pressure. To the residue, 1-butanol was added, and the mixture was refluxed. Then, 500 ml of water was added thereto, and the mixture was refluxed for 5 hours. Then, the mixture was neutralized by an addition of 15% aqueous ammonia. Formed precipitates were collected by filtration, washed with water and calcined at 400° C. for 2 hours under a dry air stream to obtain a catalyst, which is designated as Catalyst 27.

Catalyst 28

30 ml of methanol was added to 5 g of niobium pentachloride and 4.9 g of chromium (III) chloride hexahydrate. This solution was dropwise added to 300 ml of 5% aqueous ammonia. Formed precipitates were collected by filtration, washed with water and calcined at 400° C. for 2 hours under a dry air stream to obtain a catalyst, which is designated as Catalyst 28.

Catalyst 29

5 g of niobium pentachloride was dissolved in 10 ml of methanol. To this solution, 10 ml of concentrated hydrochloric acid was added. To this solution, a solution prepared by dissolving 4.5 g of manganese acetate hexahydrate in 50 ml of water, was added. Water was added thereto to bring the total volume to 300 ml. Then, 300 ml of the solution was dropwise added to 150 ml of 15% aqueous ammonia. Formed precipitates were collected by filtration, washed with water and calcined at 400° C. for 2 hours under a dry air stream to obtain a catalyst, which is designated as Catalyst 29.

Catalyst 30

5 g of niobium pentachloride was dissolved in 10 ml of methanol. To this solution, a solution prepared by dissolving 3 g of iron (III) chloride in 50 ml of water, was added. This solution was dropwise added to 550 ml of 3% aqueous ammonia. Formed precipitates were collected by filtration, washed with water and calcined at 400° C. for 2 hours under a dry air stream to obtain a catalyst, which is designated as Catalyst 30.

COMPARATIVE CATALYST A 10 g of water-containing niobium oxide (AD-378) manufactured by CBMM Co. was calcined at 400° C. for 2 hours under a dry air stream. The BET specific surface area was 99 m²/g. This was found to be not crystallized from the X-ray diffration. This was further calcined at 500° C. for 2 hours under a dry air stream to obtain a catalyst, which is designated as Comparative Catalyst A. The BET specific surface area was 17 m²/g. From the X-ray diffraction, this Comparative Catalyst was found to be crystal.

COMPARATIVE CATALYST B 130 g of lanthanum nitrate hexahydrate was dissolved in deionized water under stirring. Separately, 79.2 g of diammonium hydrogen phosphate was dissolved in deionized water under stirring. While vigorously stirring the aqueous diammonium hydrogen phosphate solution, the aqueous lanthanum nitrate solution was added at once, whereby thick bulky precipitates formed. A thick creamy suspension was obtained by stirring, and the precipitates were collected by filtration under suction. The paste-like solid thus obtained was thoroughly washed with deionized water and then dried at a temperature of from 80 to 90° C. to obtain a catalyst, which is designated as Comparative Catalyst B.

COMPARATIVE CATALYST C

To 67.6 g of aluminum oxide trihydrate, 279.4 g of 85% phosphoric acid was added portionwise in several times. The mixture was left to stand at room temperature. Before the temperature became constant, the mixture was heated abruptly to 120° C. to obtain a viscous uniform solution. The hot reaction solution was poured into distilled water under stirring to obtain a colorless transparent solution having a pH of from 2 to 3. To this solution, a 30% ammonium hydroxide solution was added, whereby white precipitates formed. Ammonium hydroxide was added until precipitates no longer formed. Then, white precipitates were collected by filtration under suction. The precipitates were thoroughly washed with distilled water and then with methanol, and then dried in an evacuated deccicator at a temperature of from 80 to 100° C. for 16 hours. Then, the precipitates were calcined at 250° C. for 7 hours to obtain aluminum phosphate, which is designated as Comparative Catalyst C.

EXAMPLE 2

1.6 g of Catalyst 1, 60.0 g of EDA and 30.0 g of MEA were charged into a 200 ml stainless steel autoclave equipped with an electromagnetic stirrer. After flushing with nitrogen, the mixture was heated to 300° C. and maintained at that temperature for 5 hours. The reaction pressure was 42.5 kg/cm²G. Then, the reaction solution was cooled and analyzed by gas chromatography. The conversion of MEA was 70.0%, and the composition of the reaction solution excluding the starting materials and formed water was as follows: PIP: 4.3% by weight, DETA: 53.1% by weight, AEEA: 3.6% by weight, AEP: 3.1% by weight, and TETA: 21.6% by weight. The recovery rate of the catalyst was 100%.

EXAMPLE 3

The reaction was conducted under the same condition as in Example 2 except that the reaction was conducted for 2.7 hours by using 3.0 g of Catalyst 1. The results are shown in Table 1.

COMPARATIVE EXAMPLE 1

The reaction was conducted under the same condition as in Example 1 except that the reaction was conducted for 3.0 hours by using 3.0 g of Comparative Catalyst C. The results are shown in Table 1.

COMPARATIVE EXAMPLE 2

The reaction was conducted under the same condition as in Example 2 except that the reaction was conducted for 3.0 hours by using 3.0 g of Comparative Catalyst B.

COMPARATIVE EXAMPLE 3

The reaction was conducted under the same condition as in Example 2 except that the reaction was conducted for 6.3 hours by using 12.0 g of silica manufactured by Nikki Kagaku K.K. as the catalyst. The results are shown in Table 1.

TABLE 1

| | Conversion of MEA (%) | Composition of the reaction product[1] | | | | | Non-cyclic TETA[2] (%) | Hydroxyl group content[3] (%) |
| --- | --- | --- | --- | --- | --- | --- | --- | --- | --- |
| | | PIP | DETA | AEEA | AEP | TETA | TEPA | | |
| Example 3 | 64.5 | 4.8 | 55.7 | 3.2 | 2.8 | 23.9 | 4.5 | 91.4 | 5.4 |
| Comparative Example 1 | 30.0 | 3.7 | 73.5 | 20.1 | 1.1 | 2.3 | 0.0 | 85.7 | 21.5 |
| Comparative Example 2 | 26.8 | 1.8 | 75.1 | 10.4 | 0.8 | 6.6 | 0.0 | 89.4 | 12.2 |
| Comparative Example 3 | 28.8 | 3.9 | 51.6 | 27.4 | 1.9 | 5.1 | 0.0 | 88.4 | 34.7 |

[1]% by weight excluding the starting materials and formed water.
[2]Gas chromatogram area %: (Branched + linear)/(Branched + linear + cyclic isomer) × 100
[3]AEEA/(AEEA + DETA) × 100

EXAMPLE 4

Into a 200 ml stainless steel autoclave equipped with an electromagnetic stirrer, 4.8 g of Catalyst 1 was charged, and 30.0 g of EDA and 15.0 g of MEA were added thereto. After flushing with nitrogen, 52.6 g of ammonia was added, and the mixture was reacted at 280° C. for 2 hours. After cooling, the reaction solution was taken out and analyzed by gas chromatography. As a result, the conversion of MEA was 62.8%, and the composition of the reaction solution excluding the starting materials and formed water was as follows: PIP: 5.1% by weight, DETA: 34.1% by weight, AEEA: 0.7% by weight, and TETA: 12.0% by weight.

EXAMPLE 5

The reaction was conducted under the same condition as in Example 2 except that 1.0 g of Catalyst 2 was used as the catalyst. The conversion of MEA was 47.1%, and the composition of the reaction solution excluding the starting materials and formed water was as follows: PIP: 2.7% by weight, DETA: 42.6% by weight, and TETA: 11.2% by weight.

EXAMPLES 6 and 7

The reactions were conducted under the same condition as in Example 2 except that as the catalyst, those as identified in Table 2 were used in the amounts as identified in Table 2, and the reactions were conducted for the periods of time as identified in Table 2. The results are shown in Table 2.

TABLE 2

| | Catalyst | Amount of catalyst (g) | Reaction time (hr) | Conversion of MEA (%) |
| --- | --- | --- | --- | --- |
| Example 6 | Catalyst 3 | 1.1 | 5.0 | 62.5 |
| Example 7 | Catalyst 4 | 6.4 | 3.0 | 50.8 |

EXAMPLES 8 AND 9

The reactions were conducted under the same condition as in Example 2 except that as the catalyst, 3.0 g of the catalysts as identified in Table 3 were used, and the reactions were conducted for the periods of time as identified in Table 3. The results are shown in Table 3.

COMPARATIVE EXAMPLE 4

The reaction was conducted under the same condition as in Example 2 except that as the catalyst, 3.0 g of Comparative Catalyst A was used, and the reaction was conducted for 3.0 hours. The results are shown in Table 3.

TABLE 3

| | Catalyst | Amount of catalyst (g) | Reaction time (hr) | Conversion of MEA (%) |
| --- | --- | --- | --- | --- |
| Example 8 | Catalyst 1 | 3.0 | 2.7 | 64.5 |
| Example 9 | Catalyst 5 | 3.0 | 2.5 | 35.4 |
| Comparative Example 4 | Comparative Catalyst A | 3.0 | 3.0 | 8.8 |

EXAMPLE 10

The reaction was conducted under the same condition as in Example 2 except that as the catalyst, 1.4 g of Catalyst 6 was used. The reaction pressure was 40.5 kg/cm$^2$G. Then, the reaction solution was cooled and analyzed by gas chromatography. The conversion of MEA was 48.3%, and the composition of the reaction solution excluding the starting materials and formed water was as follows: PIP: 3.0% by weight, DETA: 43.5% by weight, AEEA: 9.3% by weight, AEP: 1.2% by weight, and TETA: 13.6% by weight. The non-cyclic rate of TETA i.e. (branched+linear)/(branched+linear+cyclic isomer) ×100, was 85.9%.

EXAMPLE 11

The reaction was conducted under the same condition as in Example 2 except that 3.0 g of Catalyst 7 was used, and the reaction was conducted for 2 hours. The conversion of MEA was 43.2%.

EXAMPLE 12

3.0 g of Catalyst 8, 30.1 g of EDA and 15.0 g of MEA were charged into a 200 ml stainless steel autoclave equipped with an electromagnetic stirrer. After flushing with nitrogen, 55.6 g of ammonia was added, and the mixture was heated to 280° C. and maintained at that temperature for 3 hours. The reaction pressure was 357 kg/cm²G. Then, the reaction solution was cooled and analyzed by gas chromatography. The conversion of MEA was 67.8%, and the composition of the reaction solution excluding the starting materials and formed water was as follows: PIP: 3.9% by weight, DETA: 34.7% by weight, AEEA: 0.0% by weight, AEP: 4.3% by weight, and TETA: 12.8% by weight.

EXAMPLES 13 AND 14

The reactions were conducted under the same condition as in Example 2 except that as the catalyst, 3.0 g of the catalysts as identified in Table 4 were used, and the reactions were conducted for 2 hours. The results are shown in Table 4.

TABLE 4

|  | Catalyst | Reaction time (hr) | Conversion of MEA (%) |
|---|---|---|---|
| Example 13 | Catalyst 9 | 2.5 | 56.1 |
| Example 14 | Catalyst 10 | 2.5 | 43.0 |

EXAMPLE 15

The reaction was conducted under the same condition as in Example 2 except that as the catalyst, 1.5 g of Catalyst 11 was used. The reaction pressure was 36.0 kg/cm²G. Then, the reaction solution was cooled and analyzed by gas chromatography. The conversion of MEA was 26.1%, and the composition of the reaction solution excluding the starting materials and formed water was as follows: PIP: 3.7% by weight, DETA: 40.8% by weight, AEEA: 15.8% by weight, and TETA: 5.1% by weight. The recovery rate of the catalyst was 100%.

EXAMPLE 16

The reaction was conducted under the same condition as in Example 2 except that 3.0 g of Catalyst 12 was used, and the reaction was conducted for 2 hours. The results are shown in Table 5.

TABLE 5

|  | Amount of catalyst (g) | Reaction time (hr) | Conversion of MEA (%) | Non-cyclic TETA* (%) |
|---|---|---|---|---|
| Example 16 | 3.0 | 2.0 | 34.0 | 93.3 |

*Gas chromatogram area %: (Branched + linear)/(Branched + linear + cyclic isomer) × 100

EXAMPLE 17

Into a 200 ml stainless steel autoclave equipped with an electromagnetic stirrer, 3.0 g of Catalyst 13, 15.0 g of MEA and 54.4 g of ammonia were charged and reacted at 280° C. for 3 hours. The reaction solution was cooled and analyzed by gas chromatography. The conversion of MEA was 93.1%, and the composition of the reaction solution was as follows: EDA: 16.4% by weight, MEA: 6.9% by weight, PIP: 5.1% by weight, DETA: 4.9% by weight, AEEA: 0.06% by weight, and TETA: 7.8% by weight.

EXAMPLE 18

Into a 200 ml stainless steel autoclave equipped with an electromagnetic stirrer, 3.0 g of Catalyst 13, 60.0 g of EDA, 30.0 g of MEA and 16.5 g of ammonia were charged and reacted at 280° C. for 5 hours. The reaction solution was cooled and analyzed by gas chromatography. The conversion of MEA was 46.5%, and the composition of the reaction solution was as follows: EDA: 51.4% by weight, MEA: 17.8% by weight, PIP: 0.7% by weight, DETA: 14.9% by weight, AEEA: 0.4% by weight, and TETA: 2.9% by weight.

EXAMPLES 19 AND 20

The reaction was conducted under the same condition as Example 2 except that as the catalyst, 3.0 g of the catalysts as identified in Table 6 were used, and the reaction time was changed to 2.5 hours. The reaction solution was cooled and analyzed by gas chromatography. The results are shown in Table 6.

TABLE 6

|  | Catalyst | Reaction time (hr) | Conversion of MEA (%) |
|---|---|---|---|
| Example 19 | Catalyst 14 | 2.5 | 26.1 |
| Example 20 | Catalyst 15 | 2.5 | 19.5 |

EXAMPLE 21

The reaction was conducted under the same condition as in Example 2 except that as the catalyst, 1.9 g of Catalyst 16 was used. The reaction pressure was 42.5 kg/cm²G. Then, the reaction solution was cooled and analyzed by gas chromatography. The conversion of MEA was 51.8%, and the composition of the reaction solution excluding the starting materials and formed water was as follows: PIP: 2.8% by weight, DETA: 38.8% by weight, AEEA: 8.7% by weight, AEP: 1.3% by weight, and TETA: 12.7% by weight. The noncyclic rate of TETA i.e. (branched+linear)/(branched+linear+cyclic isomer) ×100, was 86.3%.

EXAMPLE 22

The reaction was conducted under the same condition as in Example 2 except that 3.0 g of Catalyst 17 was used, and the reaction was conducted for 2 hours. The conversion of MEA was 46.0%.

EXAMPLE 23

3.0 g of Catalyst 18, 30.1 g of EDA and 15.0 g of MEA were charged into a 200 ml stainless steel autoclave equipped with an electromagnetic stirrer. After flushing with nitrogen, 52.3 g of ammonia was charged thereto, and the mixture was heated to 280° C. and maintained at that temperature for 3 hours. The reaction pressure was 316 kg/cm²G. Then, the reaction solution was cooled and analyzed by gas chromatography. The conversion of MEA was 44.8%, and the composition of the reaction solution excluding the starting materials and formed water was as follows: PIP: 2.4% by weight, DETA: 33.4% by weight, AEEA: 2.3% by weight, AEP: 2.1% by weight, and TETA: 7.7% by weight.

EXAMPLES 24 AND 25

The reactions were conducted under the same condition as in Example 2 except that 3.0 g of the catalysts as identified in Table 7 were used, and the reactions were conducted for 2 hours. The reaction solutions were cooled and analyzed by gas chromatography. The results are shown in Table 7

TABLE 7

| | Catalyst | Reaction time (hr) | Conversion of MEA (%) |
|---|---|---|---|
| Example 24 | Catalyst 19 | 3.0 | 45.1 |
| Example 25 | Catalyst 20 | 3.0 | 39.3 |

EXAMPLE 26

The reaction was conducted under the same condition as in Example 2 except that 1 g of Catalyst 23 was used, and the reaction was continued for 3 hours. The reaction pressure was 90.0 kg/cm$^2$G. The reaction solution was cooled, withdrawn and analyzed by gas chromatography. As a result of the analysis, the conversion of MEA was 43.5%, and the composition of the reaction solution excluding the starting materials and formed water, was as follows: PIP: 3.41% by weight, DETA: 10.57% by weight, AEEA: 2.26% by weight, AEP: 1.63% by weight, TETA: 4.33% by weight, and TEPA: 1.13% by weight.

EXAMPLE 27

The reaction was conducted under the same condition as in Example 2 except that 1 g of Catalyst 24 was used and the reaction time was changed to 2 hours. The convension of MEA was 50.5%.

EXAMPLES 28 TO 35

The reactions were conducted under the same condition as in Example 2 except that 1 g of the catalysts as identified in Table 8 were used. The results are shown in Table 8.

TABLE 8

| | Catalyst | Conversion of MEA (%) |
|---|---|---|
| Example 28 | Catalyst 21 | 14.7 |
| Example 29 | Catalyst 22 | 40.5 |
| Example 30 | Catalyst 25 | 46.4 |
| Example 31 | Catalyst 26 | 13.4 |
| Example 32 | Catalyst 27 | 33.0 |
| Example 33 | Catalyst 28 | 16.0 |
| Example 34 | Catalyst 29 | 12.5 |
| Example 35 | Catalyst 30 | 9.9 |

We claim:

1. A process for producing an alkylenamine, which comprises reacting ammonia and/or an alkylenamine with an alkanolamine in the presence of a mixed oxide catalyst to obtain an alkylenamine having an increased number of alkylene chains over the ammonia and/or the alkylenamine as starting material, wherein said mixed oxide catalyst comprises niobium oxide and a member selected from the group consisting of titania, alumina, silica, zirconia and oxides of elements in Groups IIA, VA, VIA, IB, IIB, IIIB, VB, VIB, VIIB and VIIIB of the Periodic Table.

2. The process according to claim 1, wherein the alkylenamine as starting material is an ethylenamine.

3. The process according to claim 1, wherein the alkanolamine is an ethanolamine.

4. The process according to claim 2, wherein the alkanolamine is an ethanolamine.

5. The process according to claim 1, wherein the mixed oxide catalyst comprises niobium oxide and titania in a molar ratio of Nb/Ti of from 0.01 to 100.

6. The process according to claim 1, wherein the mixed oxide catalyst comprises niobium oxide and alumina in a molar ratio of Nb/Al of from 0.001 to 100.

7. The process according to claim 1, wherein the mixed oxide catalyst comprises niobium oxide and silica in a molar ratio of Nb/Si of from 0.001 to 100.

8. The process according to claim 1, wherein the mixed oxide catalyst comprises niobium oxide and zirconia in a molar ratio of from 0.001 to 100.

* * * * *